United States Patent
Hsu et al.

(10) Patent No.: US 9,668,903 B2
(45) Date of Patent: Jun. 6, 2017

(54) POLYMERIC POLYCENTRIC HINGE

(71) Applicant: Ossur Iceland ehf, Reykjavik (IS)

(72) Inventors: Henry Hsu, Aliso Viejo, CA (US); Gudni Ingimarsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 14/945,701

(22) Filed: Nov. 19, 2015

(65) Prior Publication Data

US 2016/0143763 A1    May 26, 2016

Related U.S. Application Data

(60) Provisional application No. 62/082,254, filed on Nov. 20, 2014.

(51) Int. Cl.
*E05D 7/00* (2006.01)
*A61F 5/01* (2006.01)
*F16C 11/04* (2006.01)

(52) U.S. Cl.
CPC .......... *A61F 5/0123* (2013.01); *A61F 5/0125* (2013.01); *F16C 11/04* (2013.01); *A61F 2005/0137* (2013.01); *A61F 2005/0139* (2013.01); *A61F 2005/0155* (2013.01); *A61F 2005/0165* (2013.01); *A61F 2005/0167* (2013.01)

(58) Field of Classification Search
CPC ... Y10T 16/547; Y10T 16/541; Y10T 16/533; Y10T 16/5335; E05D 11/0054; E05D 11/0072; E05Y 2201/10; E05Y 2201/11; A61F 5/0215; A61F 5/0123; A61F 2005/0137; A61F 2005/0139; A61F 2005/0155; A61F 2005/0165; A61F 2005/0167
See application file for complete search history.

(56) References Cited

U.S. PATENT DOCUMENTS

| | | | |
|---|---|---|---|
| 3,901,223 A | 8/1975 | May | |
| 3,902,482 A | 9/1975 | Taylor | |
| 3,923,047 A | 12/1975 | Chant | |
| 4,088,130 A | 5/1978 | Applegate | |

(Continued)

FOREIGN PATENT DOCUMENTS

| AU | 2005203062 A1 | 8/2005 |
|---|---|---|
| EP | 0 382 976 A1 | 8/1990 |

(Continued)

OTHER PUBLICATIONS

International Search Report from corresponding International PCT Application No. PCT/US2013/043322, Aug. 20, 2013.

(Continued)

*Primary Examiner* — Chuck Mah
(74) *Attorney, Agent, or Firm* — Workman Nydegger

(57) ABSTRACT

A polycentric hinge for an orthopedic device includes first and second hinge arms, and two cover plates, rather than numerous individual parts and fasteners. The first and second cover plates define a plurality of bearings and a plurality of recesses for receiving the bearings, whereby the hinge arms are mounted about the bearings and are pivotable relative to one another while encased by the first and second cover plates.

20 Claims, 9 Drawing Sheets

(56) References Cited

U.S. PATENT DOCUMENTS

| | | | |
|---|---|---|---|
| 4,493,316 A | 1/1985 | Reed et al. | |
| 4,520,804 A | 6/1985 | DiGeorge | |
| 4,524,764 A | 6/1985 | Miller et al. | |
| 4,599,998 A | 7/1986 | Castillo | |
| 4,614,454 A * | 9/1986 | Kassai | B62B 7/08 |
| | | | 16/324 |
| 4,633,867 A | 1/1987 | Kausek et al. | |
| 4,723,539 A | 2/1988 | Townsend | |
| 4,732,143 A | 3/1988 | Kausek et al. | |
| 4,791,916 A | 12/1988 | Paez | |
| 4,821,707 A | 4/1989 | Audette | |
| 4,856,501 A | 8/1989 | Castillo et al. | |
| 4,886,054 A | 12/1989 | Castillo et al. | |
| 4,890,607 A | 1/1990 | Townsend | |
| 4,940,044 A | 7/1990 | Castillo | |
| 4,961,416 A | 10/1990 | Moore et al. | |
| 4,966,133 A | 10/1990 | Kausek | |
| 4,986,264 A | 1/1991 | Miller | |
| 4,991,571 A | 2/1991 | Kausek | |
| 5,000,169 A | 3/1991 | Swicegood et al. | |
| 5,022,391 A | 6/1991 | Weidenburner | |
| 5,025,782 A | 6/1991 | Salerno | |
| 5,031,606 A | 7/1991 | Ring, Sr. | |
| 5,038,763 A | 8/1991 | Wiggins | |
| 5,038,765 A | 8/1991 | Young et al. | |
| 5,062,858 A | 11/1991 | Broeck et al. | |
| 5,078,127 A | 1/1992 | Daneman et al. | |
| 5,168,865 A | 12/1992 | Radcliffe et al. | |
| 5,222,733 A | 6/1993 | Brunty | |
| 5,230,696 A | 7/1993 | Silver et al. | |
| 5,259,832 A | 11/1993 | Townsend et al. | |
| 5,288,287 A | 2/1994 | Castillo et al. | |
| 5,333,604 A | 8/1994 | Green et al. | |
| 5,356,370 A | 10/1994 | Fleming | |
| 5,372,572 A | 12/1994 | Tamagni | |
| 5,376,134 A | 12/1994 | Biedermann | |
| RE34,818 E | 1/1995 | Daneman et al. | |
| 5,403,002 A | 4/1995 | Brunty | |
| 5,443,444 A | 8/1995 | Pruyssers | |
| 5,490,822 A | 2/1996 | Biedermann | |
| 5,658,243 A | 8/1997 | Miller et al. | |
| 5,662,596 A | 9/1997 | Young | |
| 5,674,188 A | 10/1997 | Young | |
| 5,741,221 A | 4/1998 | Wetz et al. | |
| 5,766,140 A | 6/1998 | Tillinghast, III et al. | |
| 5,772,618 A * | 6/1998 | Mason | A61F 5/0123 |
| | | | 602/16 |
| 5,891,071 A | 4/1999 | Stearns et al. | |
| 5,921,946 A | 7/1999 | Tillinghast et al. | |
| 6,074,355 A | 6/2000 | Bartlett | |
| 6,129,689 A | 10/2000 | Dibello | |
| 6,402,711 B1 | 6/2002 | Nauert | |
| 6,736,567 B1 | 5/2004 | Dibello | |
| 6,740,054 B2 | 5/2004 | Stearns | |
| 6,752,775 B2 * | 6/2004 | Seligman | A61F 5/0123 |
| | | | 602/16 |
| 6,890,314 B2 | 5/2005 | Seligman | |
| 7,044,925 B2 | 5/2006 | Castillo et al. | |
| 7,059,329 B2 | 6/2006 | Mason et al. | |
| 7,189,212 B2 | 3/2007 | Popp et al. | |
| 7,235,058 B2 | 6/2007 | Doty et al. | |
| 7,507,215 B2 | 3/2009 | Ryan | |
| 7,534,219 B2 | 5/2009 | Stearns | |
| 7,544,174 B2 | 6/2009 | Nathanson | |
| 7,578,799 B2 | 8/2009 | Thorsteinsson et al. | |
| 7,682,322 B2 | 3/2010 | Engelman | |
| 7,722,555 B2 | 5/2010 | Doty et al. | |
| 7,762,972 B2 | 7/2010 | Cho | |
| 7,811,242 B2 | 10/2010 | Seligman | |
| 7,967,765 B2 | 6/2011 | Nathanson | |
| 7,985,193 B2 | 7/2011 | Thorsteinsson et al. | |
| 8,043,243 B2 | 10/2011 | Nathanson et al. | |
| 8,062,242 B2 | 11/2011 | Ceriani et al. | |
| 8,287,476 B2 | 10/2012 | Bettiol | |
| 8,795,212 B2 * | 8/2014 | Seligman | A61F 5/0123 |
| | | | 602/16 |
| 8,939,924 B1 | 1/2015 | Paulos | |
| 9,125,730 B2 | 9/2015 | Ingimundarson et al. | |
| 2004/0054307 A1 | 3/2004 | Mason et al. | |
| 2004/0097859 A1 | 5/2004 | Stearns | |
| 2004/0167452 A1 | 8/2004 | Mason et al. | |
| 2005/0148915 A1 | 7/2005 | Nathanson et al. | |
| 2005/0148918 A1 | 7/2005 | Nathanson | |
| 2005/0192523 A1 | 9/2005 | Knecht et al. | |
| 2006/0009722 A1 | 1/2006 | Seligman | |
| 2006/0173392 A1 | 8/2006 | Turrini et al. | |
| 2006/0287624 A1 | 12/2006 | Popp et al. | |
| 2008/0108922 A1 | 5/2008 | Castillo et al. | |
| 2008/0188784 A1 | 8/2008 | Ceriani et al. | |
| 2009/0030356 A1 | 1/2009 | Maloney | |
| 2009/0182254 A1 | 7/2009 | Cho | |
| 2009/0299244 A1 | 12/2009 | Chiang et al. | |
| 2010/0049108 A1 | 2/2010 | Napholz | |
| 2010/0286579 A1 | 11/2010 | Bettiol | |
| 2011/0152736 A1 * | 6/2011 | Ng | A61F 5/0123 |
| | | | 602/16 |
| 2012/0059296 A1 | 3/2012 | Kompa | |
| 2012/0271211 A1 | 10/2012 | Bledsoe | |
| 2013/0331754 A1 | 12/2013 | Dunn et al. | |
| 2015/0223958 A1 | 8/2015 | Dunn | |
| 2016/0008157 A1 * | 1/2016 | Brookover | A61F 5/0123 |
| | | | 602/16 |

FOREIGN PATENT DOCUMENTS

| | | |
|---|---|---|
| EP | 0 413 424 A1 | 2/1991 |
| EP | 0 454 186 A2 | 10/1991 |
| EP | 0 546 330 A1 | 6/1993 |
| EP | 0 615 734 A1 | 9/1994 |
| EP | 0 693 276 A1 | 1/1996 |
| EP | 1 388 330 A1 | 2/2004 |
| EP | 1 639 970 A2 | 3/2006 |
| EP | 2 345 393 A1 | 7/2011 |
| WO | 90/14807 A1 | 12/1990 |
| WO | 99/39668 A1 | 8/1999 |
| WO | 01/10360 A1 | 2/2001 |
| WO | 2004/078078 A1 | 9/2004 |
| WO | 2009/092798 A1 | 7/2009 |
| WO | 2014/067698 A1 | 5/2014 |

OTHER PUBLICATIONS

International Search Report and Written Opinion from corresponding International PCT Application No. PCT/US2015/015358, Apr. 22, 2015.

International Search Report from PCT Application No. PCT/US2015/061480, Apr. 4, 2016.

International Search Report from PCT No. PCT/US2016/059005, Jan. 5, 2017.

* cited by examiner

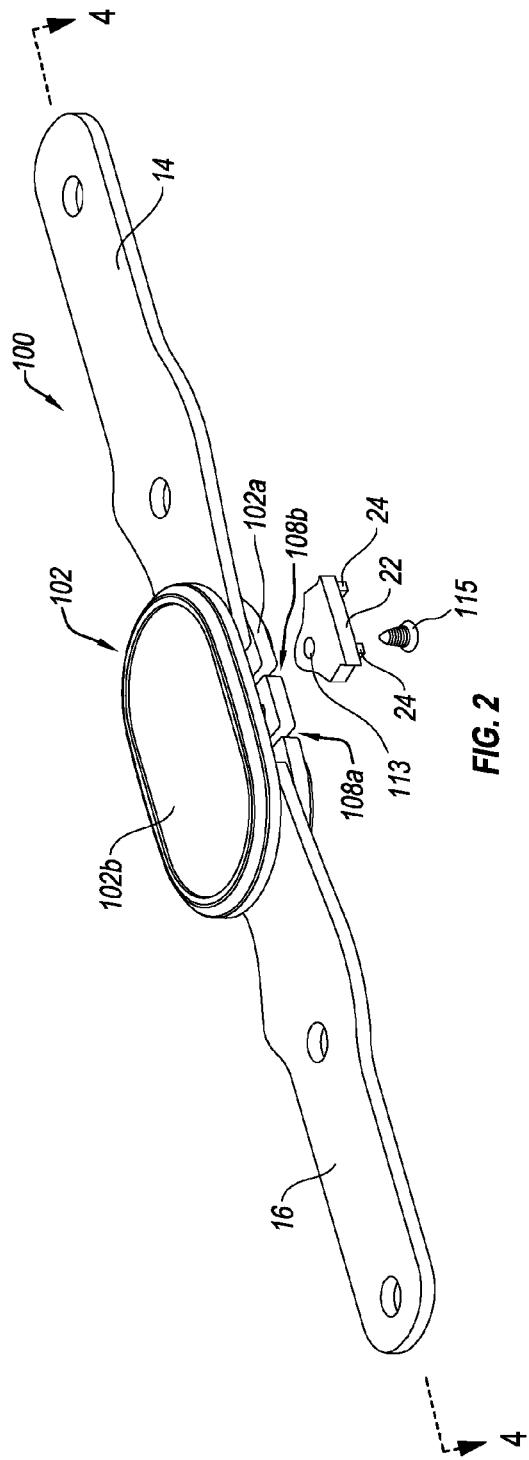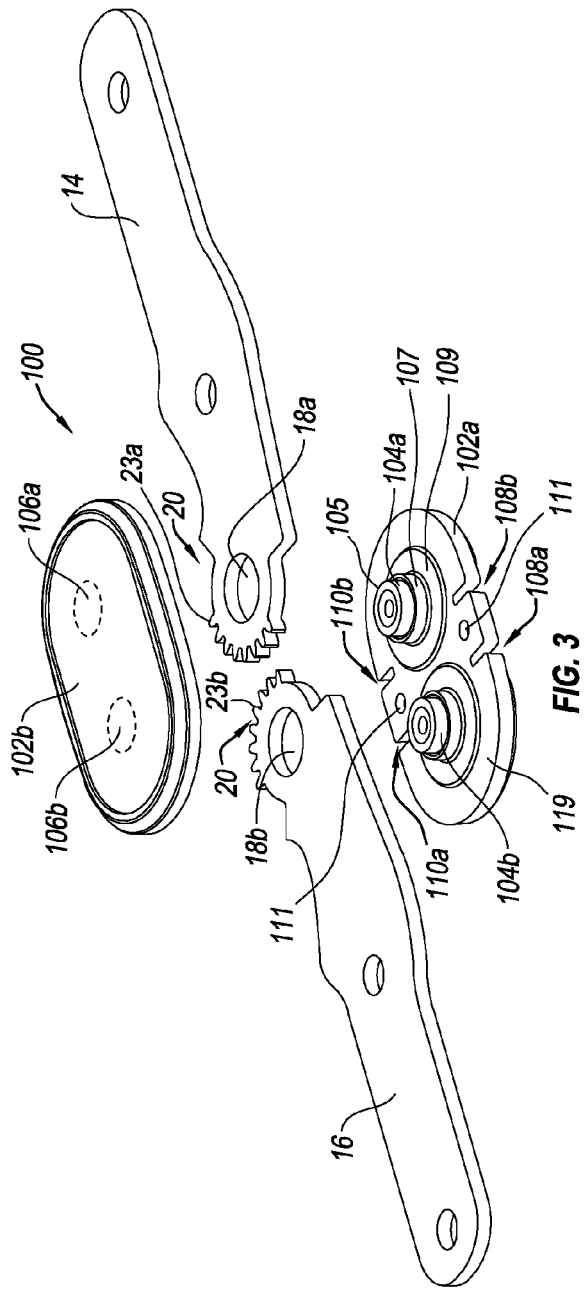
FIG. 2
FIG. 3

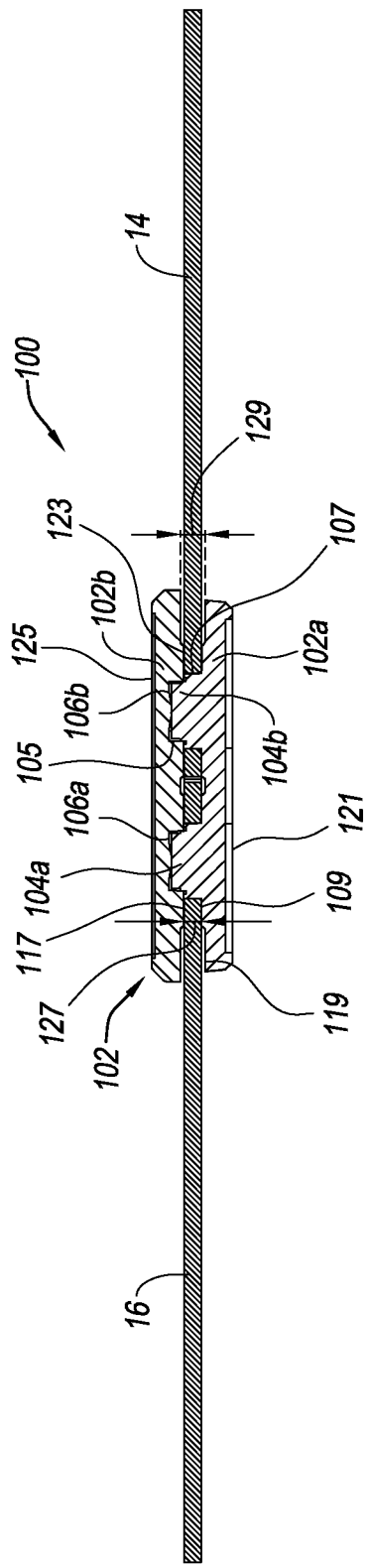
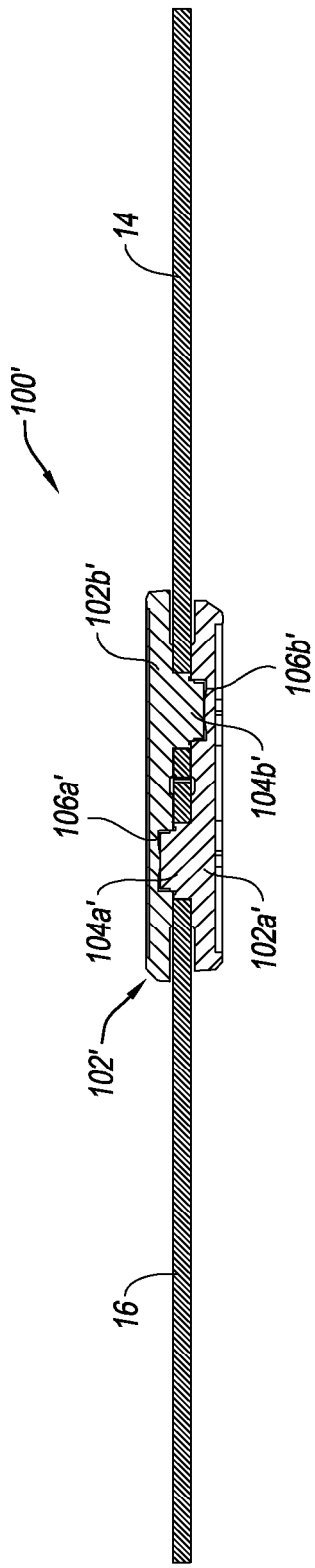

POLYMERIC POLYCENTRIC HINGE

FIELD OF THE DISCLOSURE

This disclosure relates to a polycentric hinge for an orthopedic device for supporting, limiting or controlling joint movement.

BACKGROUND

Many types of orthopedic devices include hinges that support joints, and control and limit joint movements. These joints include the knee, elbow, shoulder, hip, ankle and wrist joints.

The knee joint, although frequently considered a hinge joint, comprises two joints, lateral and medial, between the femur and tibia, and one arthrodial joint between the patella and femur. The primary movements of the knee comprise flexion, i.e., rearward rotational movement of the tibia relative to the femur, and extension, when the knee is straight and the angle between the femur bone and the tibia bone is 0 degrees.

The flexion and extension movements of the knee joint are not simply pivotal movements about a fixed axis. During flexion, the axis around which movement takes place shifts backward, and during extension it shifts forward. This differs from a more typical hinge joint, such as an elbow, where the axis of rotation does not shift. As full extension is reached, the tibia is rotated inward or rearward and the joint in effect is disposed in a "locked" position with the ligaments taut. This gives the joint greater stability in the extended position. As flexion is initiated, the tibia initially lowers or moves downwardly with small external rotation of the tibia unlocking the joint and subsequently the tibia rotates or rolls about the joint to full flexion. The initial unlocking of the knee joint during flexion precedes actual full rotation of the knee.

Because of the complexity associated with knee movement, a knee brace hinge mechanism should be able to simulate the movements of the knee. Incorporating such a hinge mechanism is important, as the knee brace must optimally support the knee joint of its user.

In post-surgical applications, the requirement for such simulation of the knee joint is important to rehabilitate and prevent re-injury of an injured knee joint. In recognizing the need for an effective post-surgical knee brace, various types of hinge mechanisms have been incorporated into known knee braces for supporting and controlling movement of the knee. One type of hinge used for duplicating movement of the human knee joint in an orthopedic device is a plural axis or polycentric hinge. As taught in U.S. Pat. Nos. 4,524,764, 4,732,143, and 5,443,444, a polycentric hinge is used to support the knee joint throughout its full range of motion, or to lock the knee joint in a selected position, or to limit the allowed range of motion of the joint to less than complete extension (straightening) and or less than complete flexion (bending) of the knee.

Because of this complexity repeat movement of the knee, the need to support the knee through a range of motion, and the ability to lock or restrict movement of knee, existing polycentric knee brace hinges are complex, including numerous parts that must be assembled together, making such devices complex and relatively expensive.

It would be an advance within the art to provide a polycentric hinge of increased simplicity, while still providing the beneficial functionality associated with existing polycentric hinge structures.

SUMMARY

In an embodiment of the present disclosure, a polycentric hinge for an orthopedic device includes a first hinge arm including a hole at a gear end thereof, and a second hinge arm including a hole at a gear end thereof, and first and second cover plates for hingedly joining the first and second hinge arms without any intermediate plates or other elements. The first and second cover plates together define a plurality of protruding tubular bearings (e.g., two bearings) and a plurality of bearing receiving recesses (e.g., two recesses). The bearings and recesses may be oppositely disposed relative to one another, to allow each bearing to be received into a corresponding recess when the cover plates are brought together, e.g., positioned over one another.

At least one of the cover plates includes at least one of the bearings, and the other of the cover plates includes the recess that corresponds to that bearing. Both bearings may be formed by the same cover plate, with the recesses in the other cover plate. As an alternative, each cover plate may include one bearing and one recess. The hole of one hinge arm is positioned over its corresponding bearing, while the hole of the other hinge arm is positioned over another bearing corresponding to that hinge arm so that when the cover plates are positioned one over the other, the bearings are inserted in the corresponding holes.

The cover plates preferably encase the gear ends of the hinge arms, maintaining the hinge arms in an orientation so gear teeth at the gear ends of the hinge arms mesh together, hingedly connecting each of the first and second hinge arms to one of the bearings. The first and second cover plates may be secured together. The cover plates may be formed of a polymeric material, and the cover plates may be ultrasonically welded together, with the bearings passing through the holes of the hinge arms, and into the recess of the opposite cover plate, holding the hinge arms meshed together, with each arm being hingedly connected to the cover plates such that they are hingedly rotatable about the bearing received through the hole of the hinge arm.

Advantageously, the bearings defined by the cover plates themselves do not necessitate additional fasteners for securing the hinge arms to the cover plates. The construction of the bearings defined by the cover plates themselves remove a requirement of additional components (i.e., fasteners or bearings) while providing a more streamlined shape to the polycentric hinge, particularly by encasing all components of the polycentric hinge between the first and second cover plates, as opposed to known polycentric hinges that include metal fasteners extending through the components of the hinge.

In constructing the polycentric hinge of the embodiments of the disclosure, outer surfaces of the cover plates are substantially smooth without interruption by any additional features, as in extraneous fasteners in the prior art. Weight is reduced since the cover plates of the polycentric hinge are preferably solely constructed from a polymeric material. Greater flexibility in adapting the polycentric hinge to various orthopedic devices is enabled since the shape and robustness can be modified by selection of polymeric materials for only the cover plates, without having to consider non-polymeric material components or other components otherwise required for making the hinge in the prior art polycentric hinges.

According to another embodiment, the polycentric hinge consists of a first hinge arm including a hole at a gear end thereof, a second hinge arm including a hole at a gear end thereof, and first and second cover plates for hingedly joining the first and second hinge arms together. One of the first and second cover plates includes protruding tubular bearings, each of which passes through a respective one of the holes of the hinge arms once assembled. The other cover plate may include bearing receiving recesses formed, so each bearing is received into a corresponding recess of the opposite cover plate when the two plates are positioned one over the other. The cover plates encase the gear ends of the first and second hinge arms, maintaining the hinge arms in an orientation so gear teeth at the gear ends of the first and second hinge arms mesh together, hingedly connecting the first and second hinge arms to the bearings. The first and second cover plates are preferably permanently secured together.

A method of manufacturing a polycentric hinge includes the steps of providing polymeric (e.g., nylon) first and second cover plates of the polycentric hinge. The cover plates collectively include a plurality of protruding tubular bearings (e.g., two bearings) and a plurality of corresponding recesses (e.g., two recesses). Each bearing is receivable within the corresponding recess when the cover plates are positioned over one another. A first hinge arm includes a hole at a gear end thereof that is positioned over its corresponding bearing of the cover plate, and a second hinge arm includes a hole at a gear end thereof that is positioned over another bearing of the cover plate.

The bearings maintain the hinge arms in an orientation so gear teeth at the gear ends of the upper and lower hinge arms mesh together, as the hinge arms are rotated about their respective bearing during use. The cover plates are brought together and positioned over one another to encase the gear ends of the hinge arms between the inner and outer cover plates, hingedly connecting the upper and lower hinge arms to a respective one of the bearings.

The disclosed orthopedic devices and associated methods of manufacture provide a simpler polycentric hinge, formed from just two parts (e.g., first and second cover plates) for joining the first and second hinge arms, which allows assembly of the polycentric hinge to be achieved faster, and in a less complex manner, with less expense. In addition, as shown, the polycentric hinges (e.g., formed of nylon or another suitable polymeric material) have been found to exhibit strength and durability characteristics equal to or better than existing polycentric hinges formed of numerous (e.g., metal) components.

Numerous other advantages, features and functions of embodiments of a polycentric hinge will become readily apparent and better understood in view of the following description and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device, and in no way limit the structures or configurations of a simplified polycentric hinge according to the present disclosure.

FIG. 2 is a perspective view showing an exemplary embodiment of a polycentric hinge according to the present disclosure.

FIG. 3 is an exploded view of the hinge in FIG. 2.

FIG. 4 is a cross-sectional view through the hinge in FIG. 2.

FIG. 4A is a cross-sectional view through an alternative embodiment of a polycentric hinge according to the present disclosure.

DETAILED DESCRIPTION OF VARIOUS EMBODIMENTS

A. Overview

Figure 1:
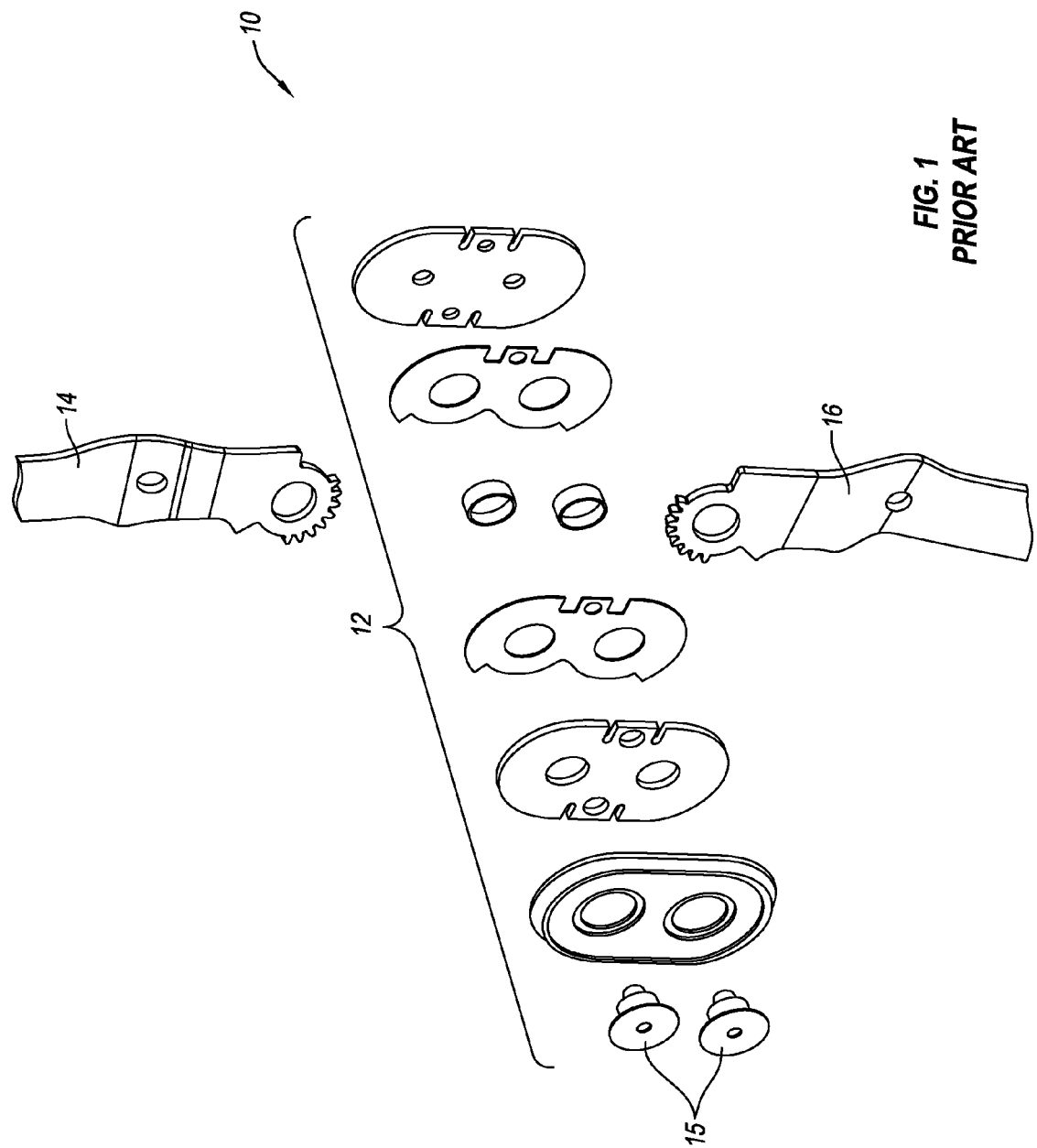
FIG. 1 is an exploded view of a prior art polycentric hinge requiring assembly of numerous parts.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intent is to cover all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning. While terms such as "first" and "second" may be used in combination with terms such as "upper" and "lower" or "inner" and "outer," the terms "first" and "second" may be used interchangeably with such terms "upper" and "lower," or "inner" and "outer," and are not necessarily limited to being associated with such terms.

Any element in a claim that does not explicitly state "means for" performing a specified function, or "step for" performing a function is not to be interpreted as a "means" or "step" clause as specified in 35 U.S.C. §112, paragraph 6.

B. Various Embodiments of a Polycentric Hinge

FIG. 1 illustrates a prior art polycentric hinge 12, which includes numerous components assembled together to form the desired hinge. The hinge 12 may serve to hingedly connect each hinge arm 14 or 16 about a respective pivot point provided by metal fasteners or pivot pins 15 used to secure components of the hinge 12 together and act as bearing surfaces about which the hinge arms rotate. The hinge 12 may include nine components fastened together; with the hinge arms 14 and 16 connected one another by the metal fasteners 15. While such a hinge provides an acceptable level of performance, it is complex and relatively expensive to manufacture.

FIGS. 2-4 illustrate an exemplary embodiment of an orthopedic device (e.g., a knee brace) according to the present disclosure that exhibits increased simplicity, streamlined shape, and reduction in weight, where the numerous components of a prior art hinge are reduced to just two cover plates 102a, 102b that may advantageously be welded (e.g., ultrasonically welded) together and support first and second hinge arms 14, 16.

The polycentric hinge 102 comprises just two cover plates, including a first or inner cover plate 102a and a second or outer cover plate 102b. Within the cover plates 102a, 102b are provided a plurality (e.g., two) of protruding tubular-shaped bearings 104a, 104b, and a plurality of recesses 106a, 106b formed by the cover plates themselves as opposed to requiring extraneous metal fasteners or pivot pins in the prior art. Each recess is oppositely disposed relative to its corresponding bearing, (e.g., recess 106a is opposite bearing 104a, and recess 106b is opposite bearing 104b) so that when the cover plates 102a and 102b are brought together, the bearings 104a and 104b are received within the corresponding recesses 106a and 106b, respectively.

The upper and lower hinge arms 14 and 16 each define a hole 18a, 18b, respectively, at a gear end 20 of each hinge arm 14 and 16. The hole 18a is positioned over the bearing 104a, so that the bearing 104a is received in, and passes through the hole 18a. Similarly, the hole 18b is positioned over the bearing 104b so that the bearing 104b is received in, and passes through the hole 18b. Upon assembly of the cover plates 102a and 102b about the hinge arms 14 and 16, the gear ends 20 of each hinge arm 14 and 16 become sandwiched or encased between cover plates 102a and 102b. The hinge arms may be formed by metal or polymeric materials, or a combination thereof. The hinge arms may be rigid or semi-rigid or may be flexible, whereby the material composition and relative rigidity of the hinge arms depends upon the usage of the hinge.

The bearings 104a, 104b are spaced apart relative to one another so the gear teeth 23a, 23b at the gear end 20 of each hinge arm 14 and 16 can mesh together. Because of such a meshed arrangement, rotation of one hinge arm about its respective bearing (e.g., arm 14 about bearing 104a) results in complementary rotation of the other hinge arm about its respective bearing (e.g., arm 16 about bearing 104b). The bearings 104a, 104b themselves serve the dual purpose as being pivot pins for the hinge arms and fasteners for securing the components of the hinge together while containing all components solely between the cover plates. Outer surfaces 121, 125 of the first and second cover plates may be substantially smooth with no extraneous components projecting therefrom, as may occur in prior art polycentric hinges. The components of the polycentric hinge are confined between the outer surfaces 121, 125.

The hinge 102 may include structural features similar to existing polycentric hinges, but only in which any such features may be integrated within the molded or otherwise formed two cover plates. As seen in FIGS. 2-4, a pair of slots 108a, 108b may be provided in one or both of the cover plates (e.g., in inner cover plate 102a) for receiving an extension stop. Such an insertable stop may not comprise a component of the hinge 102 (which comprises just two cover plates), but may be employed with the hinge to limit extension movement of the hinge arms.

An extension stop 22 (see FIG. 2) may be provided, which the stop 22 includes a pair of laterally protruding extensions 24 for receipt into the slots 108a, 108b. As shown, the slots 108a, 108b may be parallel to one another. Similarly, the protruding extensions 24 of the stop 22 may also be parallel to one another. Insertion of the stop 22 into the slots 108a, 108b may limit rotation of the hinge arms 14, 16 relative to one another, e.g., to prevent hyperextension of the knee joint (e.g., extension stop 22 may prevent rotation beyond 180°). The extension stop 22 may be configured to prevent extension beyond any desired angle.

The opposite side of hinge 102 may similarly include slots (e.g., slots 110a, 110b) for reception of a flexion stop (not shown), which may be inserted into slots 110a, 110b to limit flexion to only any desired angle (e.g., 90°). Such a flexion stop may function in a similar manner as described above relative to extension stop 22. Various extension and flexion stops will be apparent to those of skill in the art in light of the present disclosure. The stop 22 includes an aperture 113 for receiving a fastener 115 for retaining the stop 22 to the hinge 102 by insertion into an aperture 111 formed in correspondence with the 108a, 108b, which may be formed as a pair of sets on opposed sides of the cover plate 102a. Some such stops are described in further detail in U.S. patent application Ser. No. 12/877,429, incorporated herein by reference in its entirety.

As shown in FIGS. 2-4, the bearings 104a and 104b may be included within one of the cover plates (e.g., inner cover plate 102a), while the other of the cover plates (e.g., outer cover plate 102b) may include the recesses 106a and 106b. In another embodiment, the outer cover plate (e.g., disposed on the lateral side of the knee during use) may include the bearings, while the inner cover plate (e.g., disposed on the medial side of the knee during use) may include the recesses. Other embodiments are also possible.

FIG. 4 shows the bearings 104a, 104b as defining a bearing surface 109 adjacent a first surface 119 of the first cover plate 102a. The bearing surface 109 has a diameter greater than a diameter of a second portion 107 of the bearings 104a, 104b extending from the bearing surface 119. The bearing surface 109 and the second portion 107 are substantially concentric with one another.

A first portion 105 of the bearings 104a, 104b has a diameter smaller than the second portion 107. The at least one recess 106a, 106b has a diameter substantially the same as the second portion 107. The first and second portions 105, 107 and the bearing surface 109 are substantially concentric with one another, and are continuous with one another such that they are formed from the same material as the first cover plate 102a.

The second cover plate 102b defines a bearing surface 117 extending about the at least one recess 106a, 106b, and has substantially a same diameter as the bearing surface 109 of the first cover plate 102a. A first predetermined distance 127 is defined between the bearing surfaces 109, 117, when the first and second cover plates 102a, 102b are secured to one another, and generally corresponds to a thickness of the hinge arms 14, 16 against which they rotate. The bearing surface 109, 117 act as if they are washers for the first and second cover plates 102a, 102b as the hinge arms 14,16 rotate such that the first predetermined distance 127 is substantially the same of the thickness of the hinge arms 14, 16. The first and second cover plates 102a, 102b also define a clearance 129 outside of the diameters of the first and second bearing surfaces 109, 117 for permitting free rotation of the first and second hinge arms 14, 16 relative to the first and second cover plates 102a, 102b. The clearance 129 has a greater height than the first predetermined distance 127, and there is no interference from the cover plates at the clearance against the hinge arms.

FIG. 4A illustrates an alternative embodiment of a hinge 102' in which each cover plate 102a', 102b' includes a bearing (e.g., bearings 104a' and 104b', respectively), and a recess (e.g., recesses 106a', 106b') so that upon bringing the two cover plates 102a', 102b' together for placement over one another, the bearing of each cover plate is received into the recess of the opposite cover plate. The bearing 104a' may be received into the recess 106a', and the bearing 104b' is received into the recess 106b'.

The cover plates 102a and 102b may be of similar or identical shape, to provide a profile generally coextensive one with the other when the cover plates are placed over one another. As shown, the profile of each cover plate 102a, 102b may be oval in shape, so that upon placement of the two cover plates together, they are generally coextensive with one another. In an embodiment, one of the cover plates may be somewhat larger in surface area than the other. When the cover plates are oval, one of the cover plates may be a slightly larger oval than the other.

The outer cover plate 102b may be of a somewhat larger oval than the inner cover plate, so the outside perimeter of the outer cover plate covers that of the inner cover plate. The width and/or length dimensions between the two may be within about 20%, 15%, 10%, or within about 5% of one another. By way of non-limiting example, in an embodiment, the width of the inner cover plate may be about 33.5 mm, while the width of the outer cover plate may be about 36.5 mm. The length of the oval shape may similarly be somewhat larger for the outer cover plate relative to the inner cover plate, e.g., providing a small lip of the outer cover plate that extends beyond the perimeter of the inner cover plate, around the oval profile of the cover plates. Such a configuration is perhaps best apparent in FIGS. 4 and 6. The extension of the outer cover plate beyond the perimeter of the inner cover plate may be about 1.5 mm, around the entire oval perimeter. In such an embodiment, the width and length may each be about 3 mm shorter for the inner cover plate than the outer cover plate.

Rather than forming the components of the polycentric hinge from numerous separate components (e.g., formed from metal materials), the present polycentric hinge comprises just two pieces that may be formed from a polymeric material, e.g., formed by injection molding, or other suitable processes (e.g., machining, etc.). Where the two pieces (i.e., the inner and outer cover plates) are formed of such a polymer material, they may be welded together through an ultrasonic welding technique, rather than requiring joining through mechanical fasteners. In other embodiments, any other suitable technique may be employed for joining the two cover plates together (e.g., other welding techniques, use of an adhesive, etc.).

As described in further detail below, the inventors have discovered that the polycentric hinge comprised of just two pieces can be formed from a polymeric material (e.g., nylon) which may be ultrasonically welded together to provide strength and durability characteristics that are equal to or better than the current hinge configurations which employ numerous components, which components must be assembled together.

Although any suitable polymeric material may be employed, in an example, the cover plates of the hinge are formed of nylon (e.g., Nylon 6). An example of such a suitable nylon material is Hylon N2000THL, available from Ravago Manufacturing, in Brighton, Mich. Various other condensation or addition type polymers (e.g., polyolefins, polyamides, etc.) may also be suitable for use. In an embodiment, the polymeric material employed may be suitable for injection molding.

In an embodiment, the moisture content of the polymeric material may be only 0.20%, no more than 0.18%, or no more than 0.15% by weight. Such a lower moisture content (e.g., no more than 0.15%) may be achieved by drying the material for a somewhat longer period (e.g., 2-4 hours longer to reduce moisture content from 0.18% to 0.15%).

Figure 5:
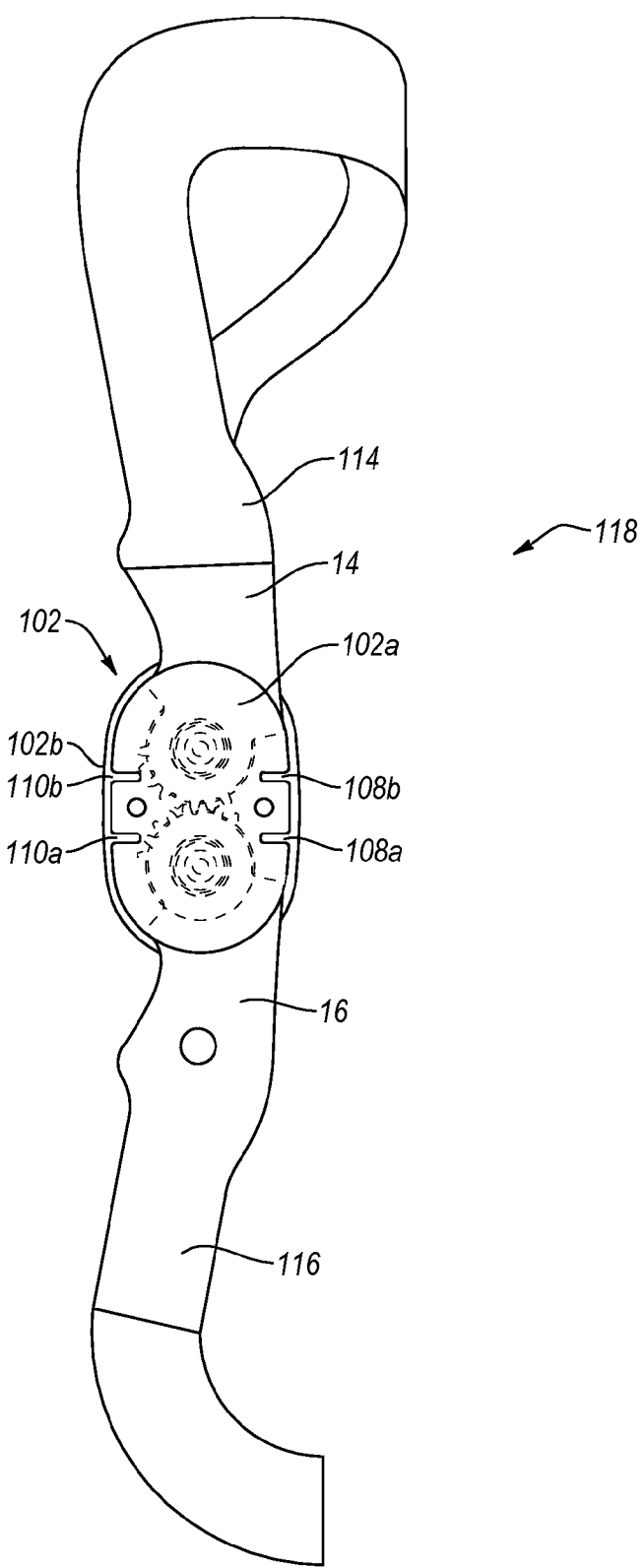
FIG. 5 is a side view showing an embodiment of a polycentric hinge where the exemplary orthopedic device is configured as a knee brace.

FIG. 5 shows an exemplary orthopedic device configured as a knee brace, where the hinge 102 is connected to the upper and lower hinge arms 14 and 16, which hinge arms are configured as the upper and lower frame portions 114, 116, respectively, of knee brace 118, as appreciated by those of skill in the art. The knee brace frame may take on many shapes, such as those shown and described in U.S. Pat. No. 5,230,697, granted Jul. 27, 1993, U.S. Pat. No. 8,048,013, granted Nov. 1, 2011, and U.S. Publication 2012/0046585, published Feb. 23, 2012, each of which is incorporated by reference in its entirety. The hinge may be considered as comprising either just the inner and outer cover plates, or first and second hinge arms secured to one another by the inner and outer cover plates, or generally comprise frame portions having the equivalent of hinge arms secured together by the inner and outer cover plates.

Figure 6:
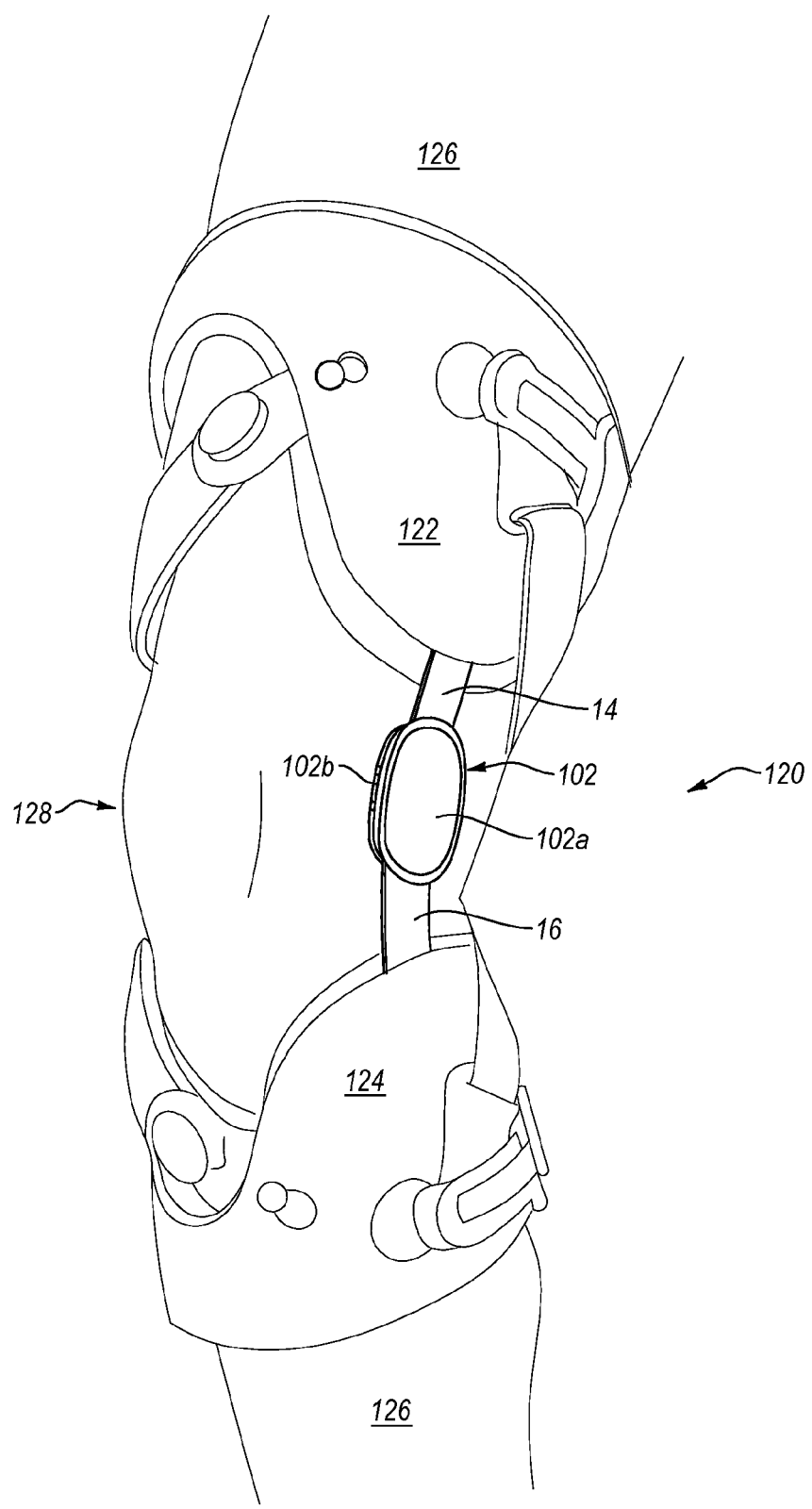
FIG. 6 is a perspective view showing another exemplary embodiment of an orthopedic device including a polycentric hinge according to the present disclosure, with the knee brace installed on a user's leg.

FIG. 6 shows another exemplary orthopedic device configured as a knee brace 120. The upper and lower hinge arms 14 and 16 are attached to the upper and lower frame portions 122 and 124, respectively of the knee brace 118, which the frame portions 122 and 124 may be secured about the upper portion of the person's leg 126 and the lower portion of the person's leg 126 (i.e., above and below the knee 128, respectively). The hinge 102 can articulate as the user's knee 128 articulates, so the knee brace supports and assists bending of the user's knee 128. It will be apparent that such a hinge may be employed in knee braces of other configurations, and other orthopedic devices (e.g., configured for placement at other joints) where it is desired to provide a hinge of increased simplicity, while still providing adequate strength and durability.

Figure 7:
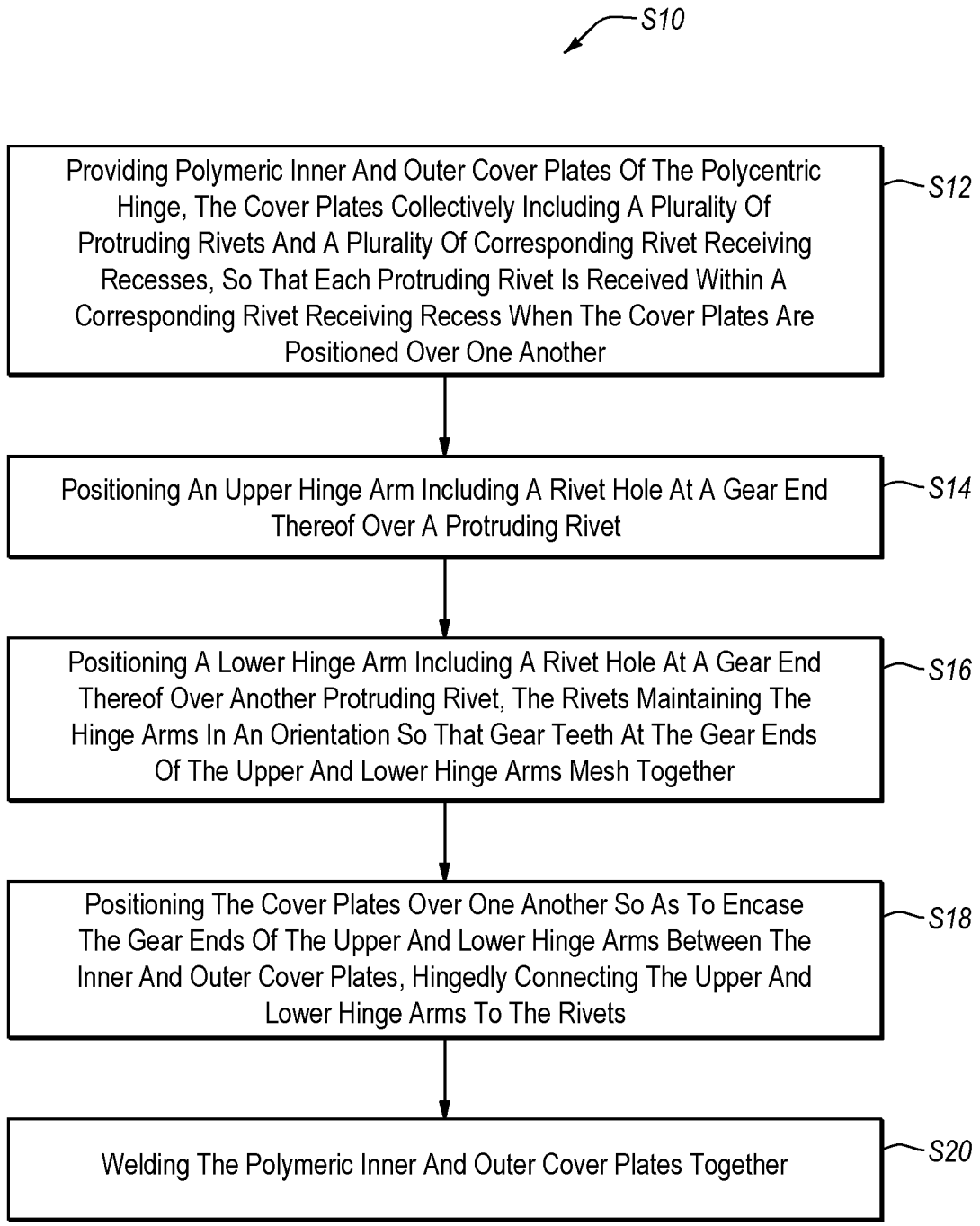
FIG. 7 is a flow chart for manufacturing the hinge of FIG. 2.

FIG. 7 shows a flow chart illustrating an exemplary method of manufacture for manufacturing the disclosed hinges comprised of a reduced number of components. As shown, an exemplary method S10 may include, at S12, providing polymeric inner and outer cover plates of the hinge, the cover plates collectively including a plurality of protruding bearings and a plurality of corresponding recesses, so that each bearing is received within a corresponding recess when the cover plates are positioned over (e.g., closed over) one another.

At S14, an upper hinge arm including a hole at a gear end thereof is positioned over a bearing of one of the cover plates. At S16, a lower hinge arm including a hole at a gear end thereof is positioned over another bearing of one of the cover plates so the bearings maintain the hinge arms in an orientation so gear teeth at the gear ends of the upper and lower hinge arms mesh together. At S18, the cover plates are positioned (e.g., closed) over one another to encase the gear ends of the upper and lower hinge arms between the inner and outer cover plates, hingedly connecting each of the upper and lower hinge arms to one of the bearings. At S20, the polymeric inner and outer cover plates are welded together.

Such welding may be achieved in an embodiment by ultrasonic welding. Any suitable ultrasonic welding technique may be employed. As described herein, the bearings (e.g., two bearings) may be provided within one of the cover plates (e.g., the inner cover plate), while the recesses may be provided within the other of the cover plates (e.g., the outer cover plate), or each cover plate may include a bearing and a recess, each configured to mate with the bearing and recess of the other cover plate (e.g., as shown in FIG. 4A). By forming the cover plates from a polymeric material such as nylon, the present inventors have discovered that the hinge advantageously may exhibit strength and durability characteristics equal to or greater than that of polycentric hinges of similar geometry, but formed of numerous components that must be assembled together, even where such components are metal, rather than polymeric. The disclosed embodiments provide for increased simplicity, while providing for equal or greater strength and durability.

To determine various strength characteristics of the nylon hinges comprised of just two cover plates, various tests were performed as described below.

D. Experimental Data

Certain tests were conducted using orthopedic devices such as that seen in FIGS. 2-4 to measure medial-lateral loading characteristics in a 3-point bend test, to measure resistance to hyperextension in an extension test, and to measure resistance to flexion beyond 90° in a flexion test.

Figure 8:
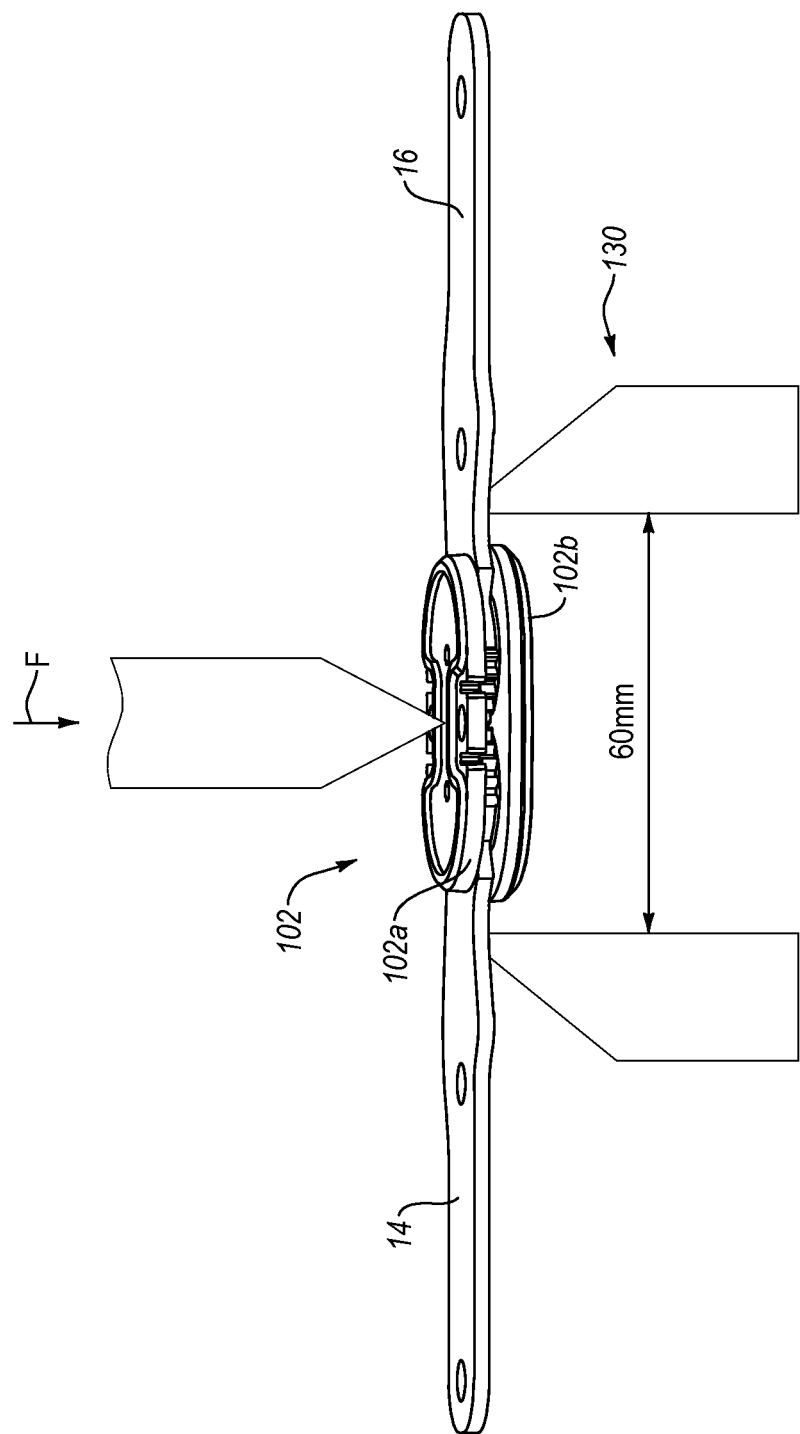
FIG. 8 schematically illustrates a test fixture used in a 3-point bend test used to test loading characteristics in the medial-lateral direction for polycentric hinges according to the present disclosure.

FIG. 8 schematically illustrates the test apparatus used in the 3-point bend test. The purpose of the test was to verify that loading characteristics of the hinge 102 in the medial-lateral direction are equal to or better than those of existing hinges assembled from numerous component parts. The hinge 102 was placed in a fixture 130 that supports each hinge arm 14 and 16 30 mm from center (for a 60 mm span). A point load F was applied until failure. Maximum load at failure was recorded, and stiffness was calculated from the slope (i.e., steady rise/run) of the load before yield. The results are presented in Table 1.

TABLE 1

| Specimen | Max Load (lb) | Stiffness (lb/in) | Pass/Fail | Comments |
|---|---|---|---|---|
| Criteria | >200 | >1200 | n/a | Based on current hinges |
| 1 | 306 | 1550 | Pass | |
| 2 | 290 | 1485 | Pass | |
| 3 | 273 | 1600 | Pass | |
| 4 | 251 | 1696 | Pass | |
| 5 | 295 | 1659 | Pass | |
| 6 | 301 | 1612 | Pass | |
| 7 | 245 | 1554 | Pass | |
| 8 | 281 | 1508 | Pass | Weld was short, double peak break |
| 9 | 296 | 1596 | Pass | |
| 10 | 308 | 1583 | Pass | |
| 11 | 306 | 1582 | Pass | |
| 12 | 279 | 1591 | Pass | |
| 13 | 256 | 1474 | Pass | |
| 14 | 285 | 1715 | Pass | |
| 15 | 223 | 1487 | Pass | |
| 16 | 262 | 1568 | Pass | |
| 17 | 216 | 1483 | Pass | Low air pressure caused short weld |
| 18 | 233 | 1485 | Pass | Low air pressure caused short weld |
| 19 | 249 | 1461 | Pass | Low air pressure caused short weld |
| 20 | 262 | 1557 | Pass | |

Figure 9:
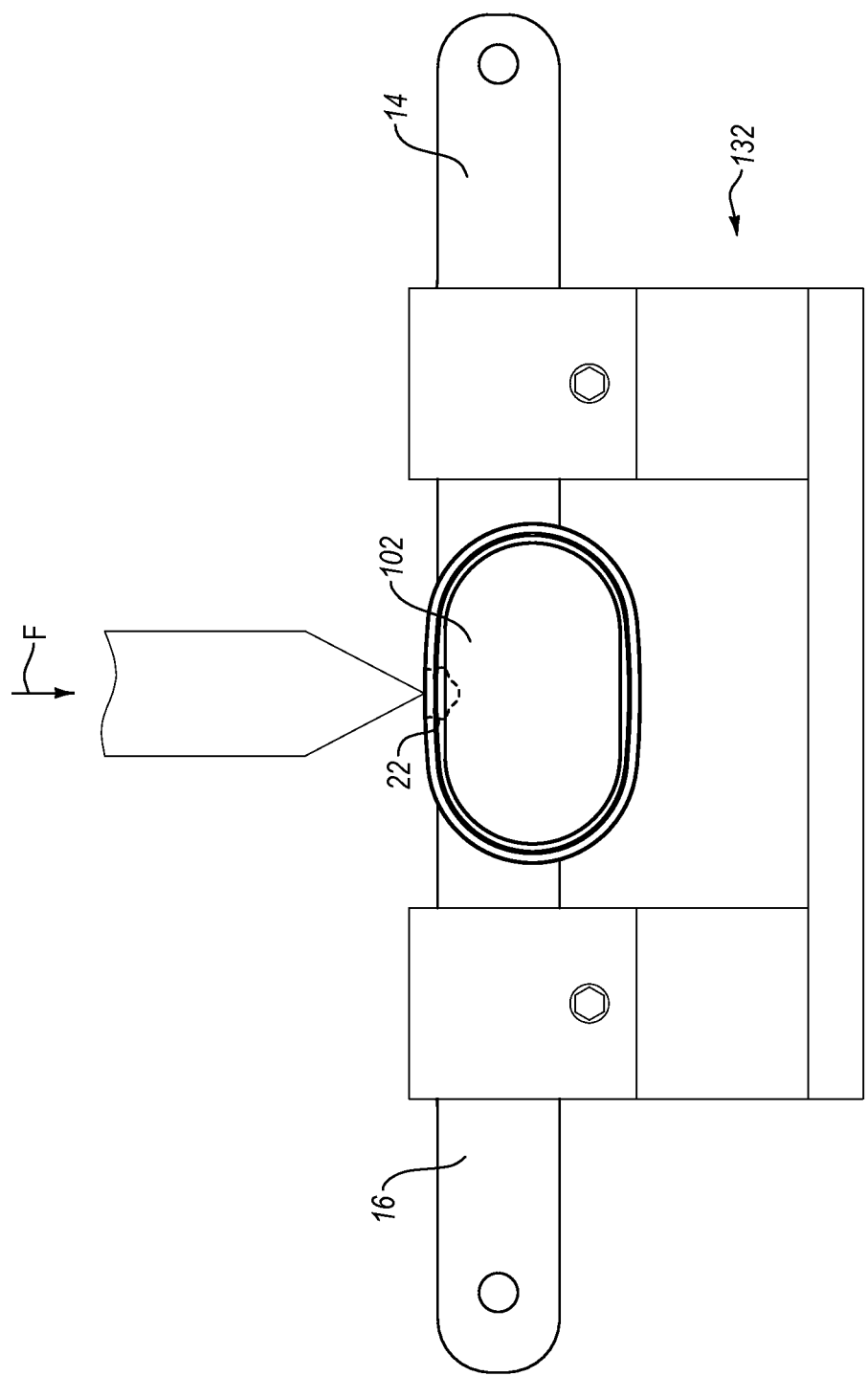
FIG. 9 schematically illustrates a test fixture used in an extension test used to test force required to force a polycentric hinge according to the present disclosure into hyperextension.

FIG. 9 schematically illustrates the test apparatus 132 used in the extension test. A hole in each hinge arm 14 and 16 was drilled 100 mm from the center of the hinge 102. The hinge 102 and hinge arms 14 and 16 were fixed into the test fixture using bolts through the hinge arms 14 and 16. Once fixed, 0° extension stops 22 (i.e., so the arms stop 180° apart from one another), were installed into hinge 102, and a point load F was applied across the extension stop 22. Maximum load at first failure was recorded. All recorded failure values are at first failure. Some specimens continued beyond first failure, and entered a phase of tensile failure, resulting in much higher loads. Specimen 1 continued until 636 lbs. The results are presented in Table 2.

TABLE 2

| Specimen | Max Load (lb) | Pass/Fail | Comments |
|---|---|---|---|
| Criteria | >100 | n/a | Based on current hinges |
| 1 | 158 | Pass | |
| 2 | 160 | Pass | |
| 3 | 156 | Pass | |
| 4 | 153 | Pass | |
| 5 | 152 | Pass | |
| 6 | 142 | Pass | |
| 7 | 154 | Pass | |
| 8 | 153 | Pass | |
| 9 | 143 | Pass | |
| 10 | 130 | Pass | |
| 11 | 142 | Pass | |
| 12 | 137 | Pass | |
| 13 | 145 | Pass | |
| 14 | 135 | Pass | |
| 15 | 149 | Pass | |
| 16 | 155 | Pass | |
| 17 | 151 | Pass | |
| 18 | 148 | Pass | |
| 19 | 143 | Pass | |
| 20 | 141 | Pass | |

Figure 10:
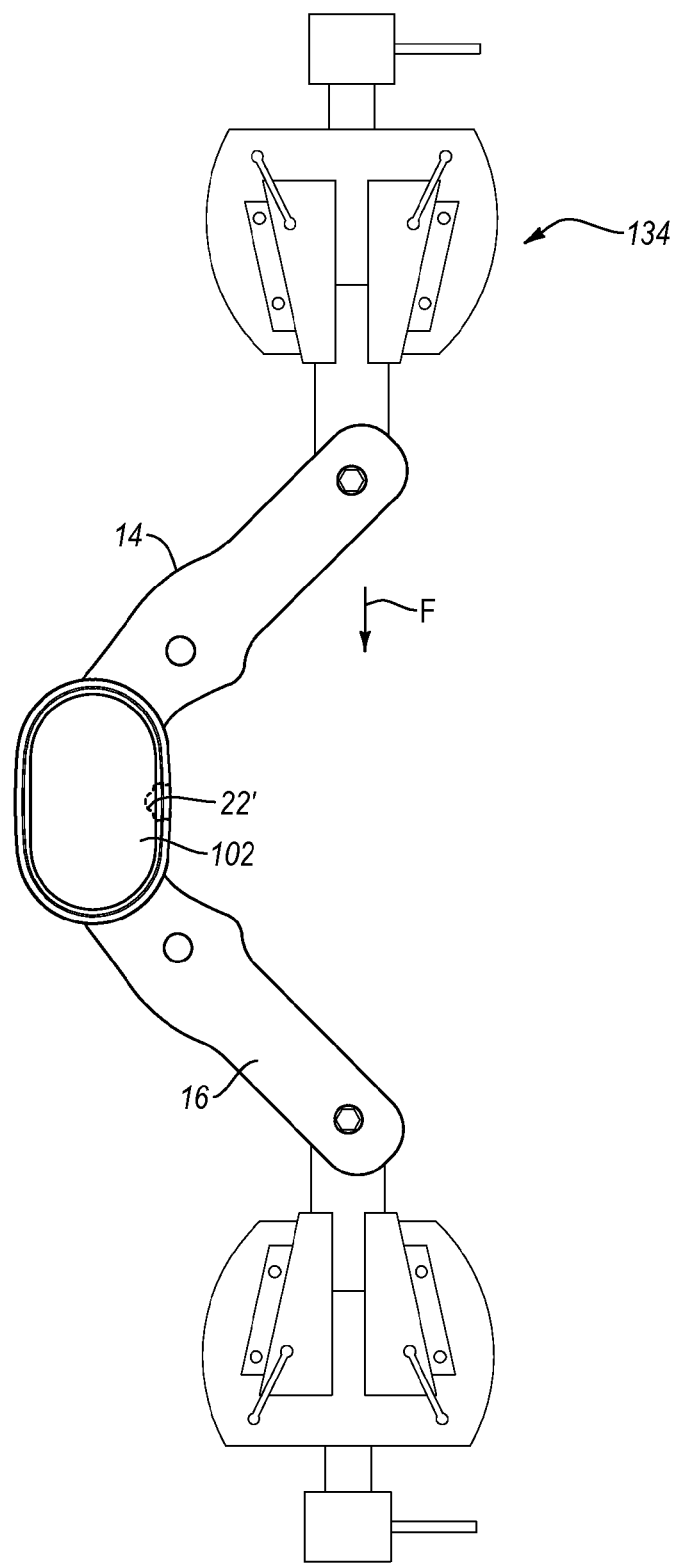
FIG. 10 schematically illustrates a test fixture used in a flexion test used to test a polycentric hinge according to the present disclosure.

FIG. 10 schematically illustrates the test apparatus 134 used in the flexion test. Flexion stops act as a sensory stop, and the required load before failure is not as high as compared to extension stops. Regardless, flexion control provides an important function for the hinge. Using current production 90° flexion stops, each hinge arm 14 and 16 was drilled 100 mm from the center of the device (i.e., center of the hinge), and fixed to an Instron machine, such that the flexion stop 22' was compressed during downward travel F of the Instron arm. Maximum load was recorded at failure. The results are presented in Table 3.

TABLE 3

| Specimen | Max Load (lb) | Pass/Fail | Comments |
|---|---|---|---|
| Criteria | >30 | n/a | Based on current hinges |
| 1 | 43 | Pass | |
| 2 | 46 | Pass | |
| 3 | 45 | Pass | |
| 4 | 45 | Pass | |
| 5 | 47 | Pass | |
| 6 | 49 | Pass | |
| 7 | 50 | Pass | |
| 8 | 47 | Pass | |
| 9 | 44 | Pass | |
| 10 | 40 | Pass | |
| 11 | 44 | Pass | |
| 12 | 48 | Pass | Tested without fixing screw |
| 13 | 50 | Pass | |
| 14 | 44 | Pass | |
| 15 | 46 | Pass | |
| 16 | 48 | Pass | |
| 17 | 46 | Pass | |
| 18 | 40 | Pass | |
| 19 | 42 | Pass | |
| 20 | 47 | Pass | |

All of the tested hinges were formed from nylon 6, with a maximum moisture content of 0.15% by weight. Through various iterations of the 3-point bend test, it was found that the maximum moisture content of 0.15% (as opposed to 0.18%) provided more consistent results than higher moisture content nylon 6. As seen in Tables 1-3, each tested specimen exhibited strength and durability characteristics at least as good, or greater than that provided by existing hinges assembled from numerous metal components, the comparative characteristics of which are shown at the top of each table.

While the foregoing embodiments have been described and shown, alternatives and modifications of these embodiments, such as those suggested by others, may be made to fall within the scope of the invention. While the orthopedic device has been described in a knee brace, it will be understood that the principles described may be extended to other types of orthopedic devices.

The invention claimed is:

1. A hinge for an orthopedic device, comprising:
a first hinge arm defining a hole at a gear end thereof;
a second hinge arm defining a hole at a gear end thereof;
first and second cover plates for hingedly joining the first and second hinge arms;
wherein the first cover plate defines first and second bearings extending from a first surface thereof and the second cover plate defines first and second recesses extending into the second cover plate from a first surface of the second cover plate for receiving a first portion of the first and second bearings, a second portion of the first and second bearings extending between the first surface of the first cover plate and the first surface of the second cover plate to maintain a predetermined distance therebetween, the first and second bearings passing through the holes of the first and second hinge arms, respectively, to enable rotation of the second hinge arm within the predetermined distance and about the second bearing relative to the first hinge arm.

2. The hinge of claim 1, wherein the first and second cover plates encase the gear ends of the first and second hinge arms to maintain the hinge arms in an orientation in which the gear teeth at mesh together, and hingedly connect the first and second hinge arms, the first and second hinge arms are mounted and rotatable about the first and second bearings defined by at least one of the first and second cover plates.

3. The hinge of claim 1, wherein the first and second cover plates are ultrasonically welded together.

4. The hinge of claim 1 wherein the first and second cover plates are solely formed from a polymeric material.

5. The hinge of claim 4, wherein the polymeric material from which the first and second cover plates are formed comprises nylon.

6. The hinge of claim 5, wherein the nylon has a maximum moisture content of 0.18% by weight.

7. The hinge of claim 5, wherein the nylon has a maximum moisture content of 0.15% by weight.

8. The hinge of claim 1, wherein the bearings are defined solely by one of the first and second cover plates and the recesses are defined solely by another one of the cover plates.

9. The hinge of claim 1, wherein the first cover plate defines a flexion/extension stop retention feature arranged for receiving a stop.

10. The hinge of claim 9, wherein the flexion/extension stop feature includes first and second slots extending from a periphery of the first cover plate, and an aperture defined between the first and second slots, the flexion/extension stop having first and second extensions for sliding into the first and second slots, and a hole for receiving a fastener and engaging the first cover plate.

11. The hinge of claim 1, wherein the bearings are solely confined between the first and second cover plates.

12. The hinge of claim 1, wherein the first and second bearings each defines a bearing surface adjacent the first surface of the first cover plate and has a diameter greater than a diameter of the second portion extending from the first surface of the first cover plate, the bearing surface and the second portion being substantially concentric with one another.

13. The hinge of claim 12, wherein the first portion has a diameter smaller than the second portion, the at least one recess having a diameter substantially the same as the second portion, the first and second portions being substantially concentric with one another.

14. The hinge of claim 13, wherein the second cover plate defines a bearing surface extending from a first surface of the second cover plate about the at least one recess, and having substantially a same diameter as the bearing surface of the first cover plate and is generally concentric with the at least one recess.

15. The hinge of claim 14, wherein the first and second cover plates define a clearance located between the first surfaces thereof for permitting free rotation of the first and second hinge arms relative to the first and second cover plates.

16. A hinge for an orthopedic device, consisting:
a first hinge arm defining a hole at a gear end thereof;
a second hinge arm defining a hole at a gear end thereof;
first and second cover plates for hingedly joining the first and second hinge arms;
wherein the first cover plate defines first and second bearings extending from a first surface thereof and the second cover plate defines first and second recesses extending into the second cover plate from a first surface of the second cover plate for receiving a first portion first and second bearings, a second portion of the at least one bearing extending between the first surface of the first cover plate and the first surface of the second cover plate to maintain a predetermined distance therebetween, the first and second bearings passing through one of the holes of the first and second hinge arms, respectively, to enable rotation of the second hinge arm within the predetermined distance and about the second bearing relative to the first hinge arm.

17. The hinge of claim 16, wherein the the first and second bearings define a bearing surface adjacent the first surface of the first cover plate and has a diameter greater than a diameter of the second portion extending from the bearing surface, the bearing surface and the second portion being substantially concentric with one another.

18. The hinge of claim 17, wherein the first portion has a diameter smaller than the second portion, the first and second recesses have a diameter substantially the same as the second portion, the first and second portions being substantially concentric with one another.

19. The hinge of claim 18, wherein the second cover plate defines a bearing surface extending about the first and second recesses, and having substantially a same diameter as the bearing surface of the first cover plate.

20. A method of manufacturing a hinge, the method comprising steps of:
providing polymeric first and second cover plates of the hinge, the first cover plate including first and second bearings and the second plate defines first and second recesses, the first and second bearings being receivable within a corresponding one of the first and second recesses when the first and second cover plates are positioned over one another;

positioning a first hinge arm including a hole at a gear end thereof over the first bearing of the first cover plate;

positioning a second hinge arm including a hole at a gear end thereof over the second bearing, the first and second bearings maintaining the first and second hinge arms in an orientation so that gear teeth at the gear ends of the first and second hinge arms mesh together;

positioning the cover plates over one another so as to encase the gear ends of the first and second hinge arms between the first and second cover plates, hingedly connecting each of the first and second hinge arms to the first and second bearings; and securing the first and second cover plates together.

* * * * *